United States Patent
Zou et al.

(10) Patent No.: US 9,089,266 B2
(45) Date of Patent: Jul. 28, 2015

(54) TILTED DETECTOR ARRAY FOR MEDICAL IMAGING SYSTEMS INCLUDING COMPUTED TOMOGRAPHY

(71) Applicants: KABUSHIKI KAISHA TOSHIBA, Minato-ku (JP); Toshiba Medical Systems Corporation, Otawara-shi (JP)

(72) Inventors: Yu Zou, Naperville, IL (US); Sachin S. Junnarkar, Mundelein, IL (US); Miesher L. Rodrigues, Buffalo Grove, IL (US); Xiaolan Wang, Buffalo Grove, IL (US)

(73) Assignees: KABUSHIKI KAISHA TOSHIBA, Minato-ku (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 217 days.

(21) Appl. No.: 13/866,798

(22) Filed: Apr. 19, 2013

(65) Prior Publication Data
US 2014/0314196 A1 Oct. 23, 2014

(51) Int. Cl.
*A61B 6/03* (2006.01)
*A61B 6/00* (2006.01)

(52) U.S. Cl.
CPC .............. *A61B 6/032* (2013.01); *A61B 6/035* (2013.01); *A61B 6/42* (2013.01); *A61B 6/4233* (2013.01); *A61B 6/4266* (2013.01); *A61B 6/4275* (2013.01); *A61B 6/4429* (2013.01); *A61B 6/4241* (2013.01); *A61B 6/482* (2013.01)

(58) Field of Classification Search
CPC ............ A61B 6/03; A61B 6/032; A61B 6/42; A61B 6/4208; A61B 6/4233; A61B 6/4266; A61B 6/4275
USPC ............................... 378/19, 98.8; 250/370.09
See application file for complete search history.

(56) References Cited

U.S. PATENT DOCUMENTS

| | | | |
|---|---|---|---|
| 4,415,808 A | | 11/1983 | Cusano et al. |
| 4,417,354 A | * | 11/1983 | Pfeiler ............................ 378/19 |
| 5,757,878 A | * | 5/1998 | Dobbs et al. .................... 378/19 |
| 5,781,606 A | * | 7/1998 | Dobbs et al. .................... 378/19 |

(Continued)

OTHER PUBLICATIONS

P.M. Shikhaliev. Tilted angle CZT detector for photon counting/energy weighting x-ray and CT imaging. Institute of Physics Publishing. Aug. 15, 2006. Web. Sep. 13, 2011. <_http://iopscience.iop.org>.

(Continued)

*Primary Examiner* — Allen C. Ho
(74) *Attorney, Agent, or Firm* — Oblon, McClelland, Maier & Neustadt, L.L.P.

(57) ABSTRACT

A medical imaging system can include a frame that has a bore that has a central longitudinal axis that intersects a target area for imaging, and a radiation source to emit radiation in radial directions towards the target area to form a fan or cone of emitted radiation that irradiates a cross-section of the target area with respect to the longitudinal axis. The system can include one or more detector arrays including a plurality of detector segments that extend along a detector axis that extends in a direction that is effectively parallel to the longitudinal axis, such that radiation emitted from the radiation source passes through the target area and is incident on one or more of the detector segments. The detector segments can each include a detecting surface that is tilted such that the detecting surface has a tilt (e.g., a non-zero slope) with respect to the detector axis.

20 Claims, 13 Drawing Sheets

(56) References Cited

U.S. PATENT DOCUMENTS

| | | | |
|---|---|---|---|
| 6,229,869 B1 * | 5/2001 | Hu ................................... | 378/4 |
| 6,335,957 B1 | 1/2002 | DiBianca | |
| 6,400,791 B1 * | 6/2002 | Schwarz ......................... | 378/17 |
| 6,580,777 B1 * | 6/2003 | Ueki et al. ...................... | 378/17 |
| 6,658,081 B2 * | 12/2003 | Bruder et al. ................... | 378/15 |
| 6,975,699 B2 * | 12/2005 | Kresse ............................ | 378/19 |
| 7,016,459 B2 * | 3/2006 | Ellenbogen et al. ............ | 378/19 |
| 7,020,236 B2 * | 3/2006 | Shechter ......................... | 378/17 |
| 7,039,154 B1 * | 5/2006 | Ellenbogen et al. ............ | 378/19 |
| 7,046,761 B2 * | 5/2006 | Ellenbogen et al. ............ | 378/57 |
| 7,106,825 B2 * | 9/2006 | Gregerson et al. ............. | 378/19 |
| 7,108,421 B2 * | 9/2006 | Gregerson et al. ............. | 378/197 |
| 7,136,452 B2 * | 11/2006 | Spartiotis et al. ............... | 378/19 |
| 7,164,747 B2 * | 1/2007 | Ellenbogen et al. ............ | 378/19 |
| 7,224,765 B2 * | 5/2007 | Ellenbogen ..................... | 378/19 |
| 7,333,589 B2 * | 2/2008 | Ellenbogen et al. ............ | 378/57 |
| 7,352,841 B2 * | 4/2008 | Ellenbogen et al. ............ | 378/19 |
| 7,440,537 B2 * | 10/2008 | Ellenbogen et al. ............ | 378/19 |
| 7,453,977 B2 | 11/2008 | DiBianca et al. | |
| 7,453,978 B1 | 11/2008 | DiBianca et al. | |
| 7,564,945 B2 * | 7/2009 | Kim ................................. | 378/65 |
| 8,098,795 B2 * | 1/2012 | Nowak et al. .................. | 378/98.8 |
| 8,466,423 B2 * | 6/2013 | Hackenschmied et al. ........................ | 250/370.09 |
| 8,693,621 B2 * | 4/2014 | Thran et al. .................... | 378/17 |
| 8,824,625 B2 * | 9/2014 | Ullberg ........................... | 378/19 |

OTHER PUBLICATIONS

P.M. Shikhaliev. Computed tomography with energy-resolved detection: a feasibility study. Institute of Physics Publishing. Feb. 19, 2008. Web. Mar. 22, 2011. <http://iopscience.iop.org>.

Fritz, Shannon (2011). Characterization of Photon Counting CZT Detectors for Medical X-ray Imaging and Spectroscopy (Doctorate Dissertation). Louisiana State University.

* cited by examiner

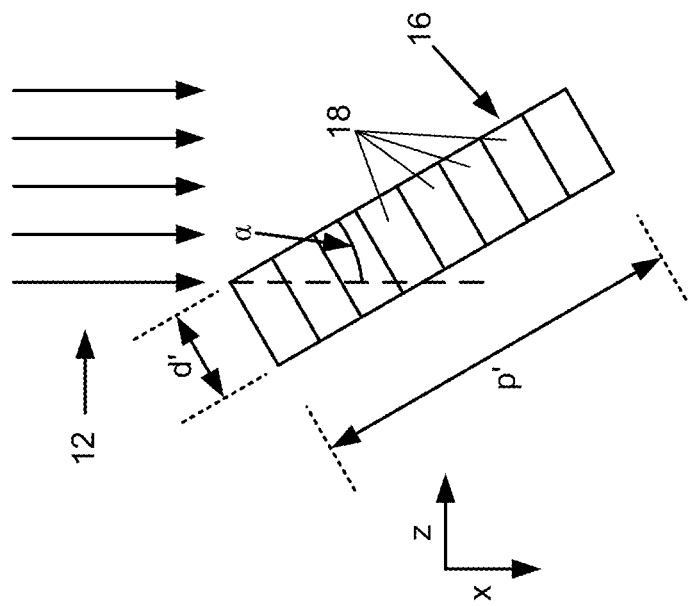
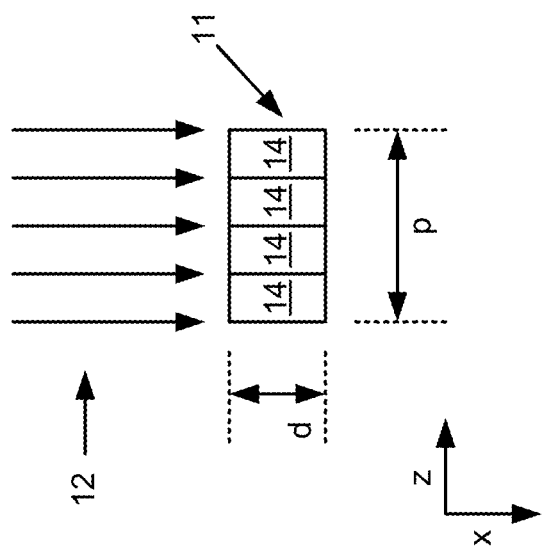

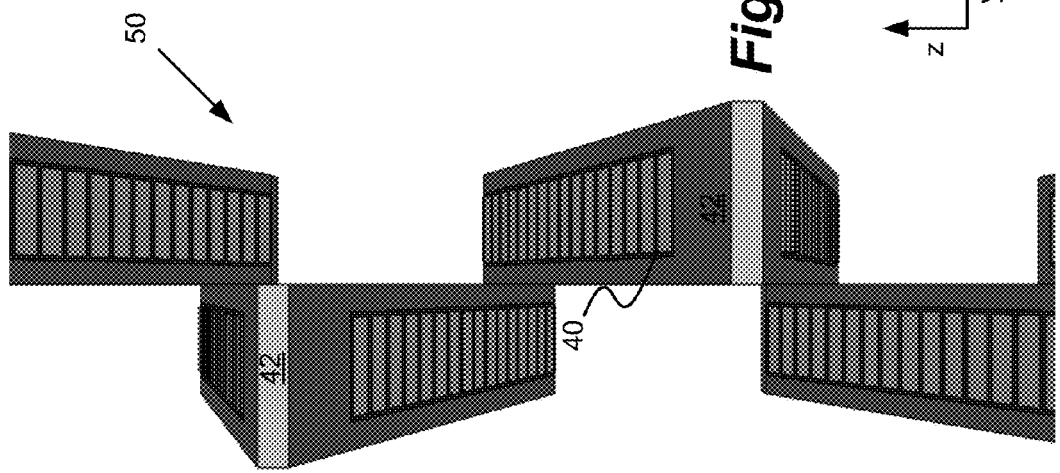
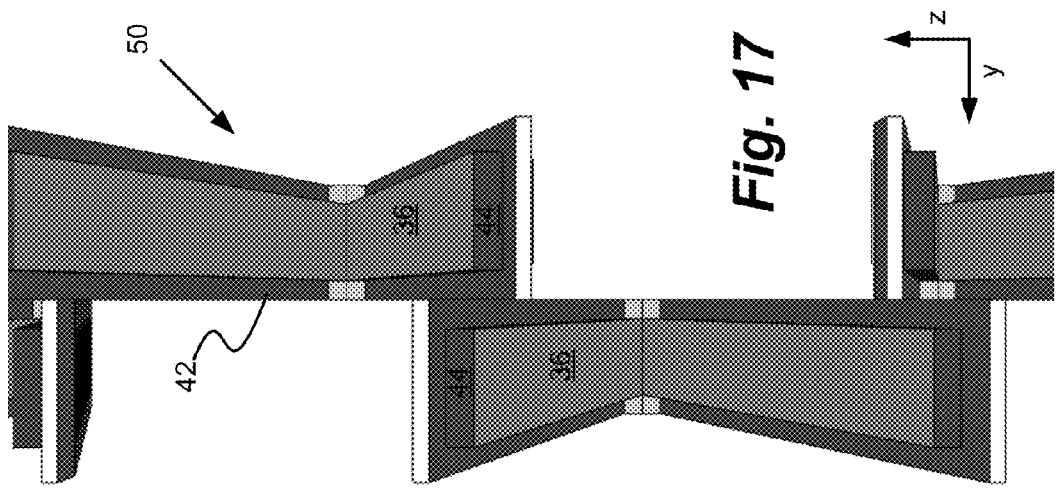

TILTED DETECTOR ARRAY FOR MEDICAL IMAGING SYSTEMS INCLUDING COMPUTED TOMOGRAPHY

FIELD

The exemplary implementations described herein generally relate to spectral computed tomography (CT) systems.

BACKGROUND

X-ray tomographic imaging, in its simplest expression, is an X-ray beam traversing an object, and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-rays from the generator, the details of the geometry and characteristics of the detector and the capacity of the acquisition system are all elements that affect how reconstruction is performed.

In one of many possible geometries, an X-ray source on top of the graph shown in FIG. 1 is emitting an X-ray beam forming a fan or cone, traversing the object. While a wide range of values can exist, typically, the distance "C" is around 100 cm, "B" is around 60 cm, and "A" is around 40 cm. In tomography, each point of the object can be traversed by a collection of rays covering at least 180 degrees. Thus, the entire X-ray generator and detector assembly can rotate around the patient. Mathematical considerations show that tomographic conditions are met when a scan of 180 degrees plus a fan angle is performed.

Conventional X-ray detectors integrate the total electrical current produced in a radiation sensor, and disregard the amplitude information from individual photon detection events. Since the charge amplitude from each event is proportional to the photon's detected energy, this acquisition provides no information about the energy of individual photons, and is thus unable to capture the energy dependence of the attenuation coefficient in the object.

On the other hand, semiconductor X-ray detectors that are capable of single photon counting and individual pulse-height analysis may be used. These X-ray detectors are made possible by the availability of fast semiconductor radiation sensor materials with room temperature operation and good energy resolution, combined with application-specific integrated circuits (ASICs) suitable for multi-pixel parallel readout and fast counting.

With such photon-counting detectors, when combined with pulse-height analysis readout, spectral information can be obtained about the attenuation coefficient in the object. A conventional CT measures the attenuation at one average energy only, while in reality, the attenuation coefficient strongly depends on the photon energy. In contrast, with pulse-height analysis, a system is able to categorize the incident X-ray photons into several energy bins based on their detected energy. This spectral information can effectively improve material discrimination and target contrast, all of which can be traded for a dose reduction to a patient.

Such photon-counting detectors for medical CT applications conventionally use a very high X-ray flux in most CT tasks. In a routine CT scan, as many as $10^8$ photons, or even more, can hit one detector element every second. Accordingly, photon-counting detectors can suffer from count loss under high rate X-ray irradiation, e.g., in a clinical CT scan. Photon count loss may occur due to, e.g., detector crystal polarization or pulse pileup.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 4 is a schematic illustration of a non-tilted detector;

FIG. 5 is a schematic illustration of a tilted detector;

FIGS. 16-18 illustrate various views of an exemplary implementation of a tilted detector including staggered V-shaped segments.

DETAILED DESCRIPTION

Figure 1:
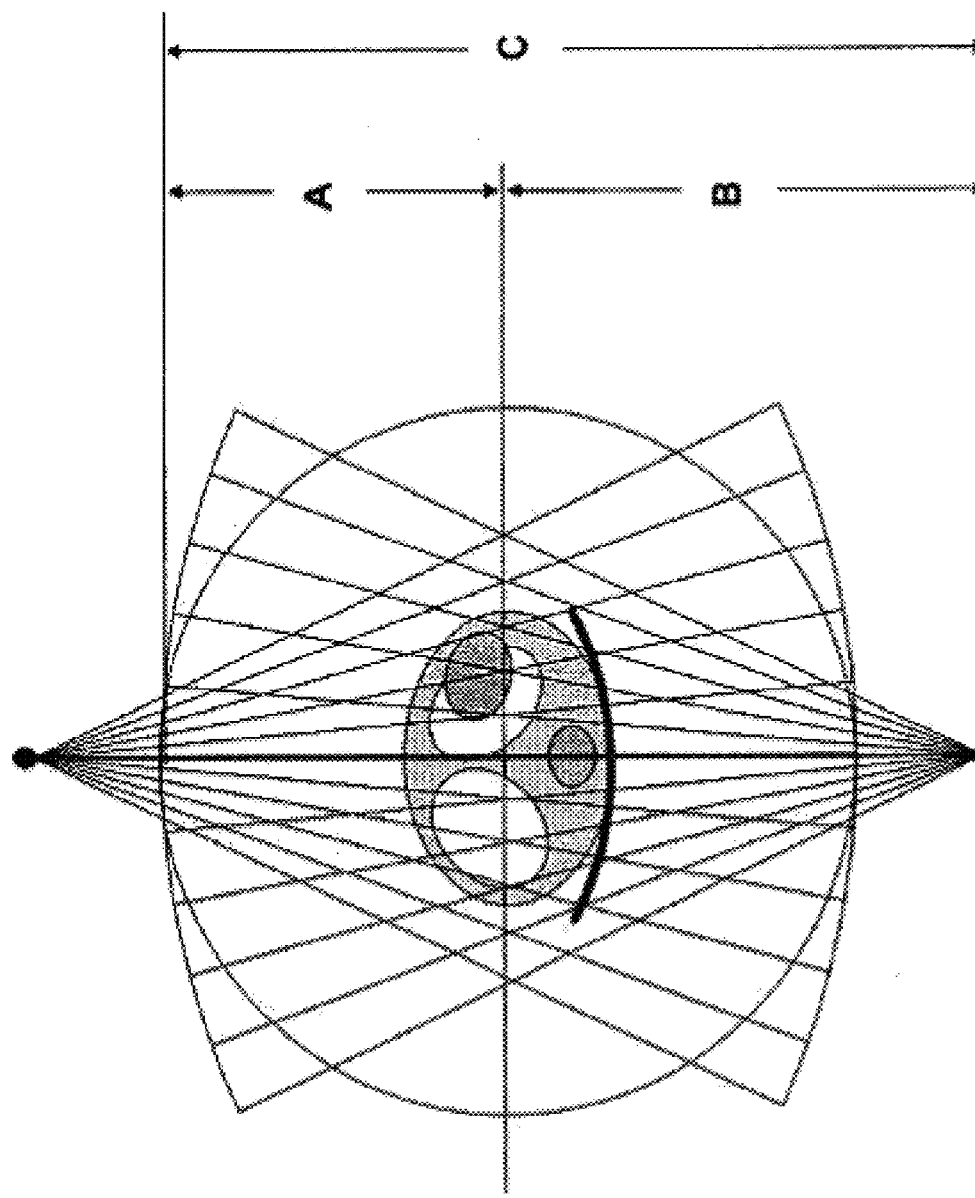
FIG. 1 illustrates an X-ray source emitting an X-ray beam forming a fan or cone, traversing an object.

According to exemplary implementations, a medical imaging system can include a frame that includes a bore that has a central longitudinal axis that intersects a target area for imaging, and a radiation source to emit radiation in radial directions towards the target area to form a fan or cone (collectively referred to as a fan or cone herein) of emitted radiation that irradiates a cross-section of the target area with respect to the longitudinal axis. The system can include a detector array including a plurality of detector segments that extend along a detector axis that extends in a direction that is generally parallel to the longitudinal axis, the detector segments arranged such that radiation emitted from the radiation source passes through the target area and is incident on one or more of the detector segments. The detector segments of the detector array can each include a detecting surface that is tilted such that the detecting surface has a tilt (e.g., a non-zero slope) with respect to the detector axis.

Pairs of adjacent detector segments of the detector array can have a side profile with a shape of a V or an upside-down V (or M, W, or upside-down M or W). Each of the pairs of adjacent detector segments can include a first detector segment that has a first detecting surface with a first tilt (a first slope) with respect to the detector axis, a second detector segment that has a second detecting surface with a second tilt (a second slope) with respect to the detector axis. The first and second tilts (slopes) can be equal in magnitude and opposite in direction. The first and second detector segments of each of the pairs of adjacent detector segments of the detector array can be joined to form an apex, with the first and second detector segments extending away from the apex. The first and second detecting surfaces can be respectively tilted by tilt angles of +α and −α with respect to a perpendicular line that intersects the apex and extends between the longitudinal axis to the detector axis, where 0°<α<90°.

The detector segments can staggered with respect to the detector axis, such that first and second sets of the detector segments are provided, respectively, on opposing first and second sides of the detector axis. First detecting surfaces of the first set can have a common first tilt (slope) with respect to the detector axis, and second detecting surfaces of the second set can have a common second tilt (slope) with respect to the detector axis. The first and second tilts (slopes) can be equal in magnitude and opposite in direction. A side profile of a detector segment of the first set and an adjacent detector segment of the second set can have a shape of a V or an upside-down V (or M, W, or upside-down M or W). The side profile can form an apex, with adjacent detector segments extending away from the apex. Detecting surfaces of the adjacent detector segments can be respectively tilted by tilt angles of +α and −α with respect to a perpendicular line that intersects the apex and extends between the longitudinal axis to the detector axis, where 0°<α<90°.

A side-profile of detector segment pairs of the first set can also form a shape of a V or an upside-down V (or M, W, or upside-down M or W). A side-profile of detector segment pairs of the second set can also form the (same) shape. The (same) shape can include a first detecting surface having a slope with respect to the detector axis +m and a second detecting surface having a slope with respect to the detector axis of −m. The side profile of the detector segments pairs of the first and second sets can form an apex, with adjacent detector segments extending away from the apex. Detecting surfaces of the adjacent detector segments can be respectively tilted by tilt angles of +α and −α with respect to a perpendicular line that intersects the apex and extends between the longitudinal axis to the detector axis, where 0°<α<90°.

A plurality of detector arrays can be arranged circularly about the longitudinal axis so as to surround at least a portion of the target area, wherein a detector axis of each of the detector arrays extends in a direction that is generally parallel to the longitudinal axis. Each of the detector arrays can include a respective set of detector segments that each includes a detecting surface that is tilted such that the detecting surface has a tilt or slope with respect to the detector axis. The plurality of detector arrays can extend circularly so as to encompass only an arc of space that coincides with the fan or cone of emitted radiation, so as to encompass only a wedge portion of the frame/bore of the medical imaging system, where the radiation source and the plurality of detector arrays can be coupled together so as rotate together about the longitudinal axis. In another implementation, the radiation source can be arranged to rotate around the longitudinal axis in a circle, where the plurality of detector arrays extend circularly so as to encompass a full range of different alignments for the fan or cone of emitted radiation as the radiation source rotates around the longitudinal axis in the circle, while the plurality of detector arrays remain stationary with respect to the target area.

The plurality of detector arrays can be angularly and regularly spaced apart, such that a radial angle of a radial line that extends from the longitudinal axis to respective detector axis changes by a constant amount between adjacent detector arrays.

At least one of the target area and the radiation source can be rotatable relative to the other about a longitudinal axis A detector for detecting radiation in a medical imaging system that includes a frame that has a bore can be provided. The detector can include a detector array including a plurality of detector segments that extend along a detector axis that extends in a direction that is generally, substantially or effectively parallel to a longitudinal axis of the bore of the medical imaging system. The detector segments of the detector array can each include a detecting surface that is tilted such that the detecting surface has a slope with respect to the detector axis and the longitudinal axis. The slope of detecting surfaces of adjacent detector segments of the detector array can vary so that a tilt angle between the detecting surfaces varies between the adjacent detector segments in a direction along the detector axis.

The detecting surface of a detector segment can include a detector electrode that is a continuous cathode. On an opposing side of the cathode, pixilated anode can be provided.

Shields formed of shielding material can be provided at ends of the detecting surface to cover or inhibit radiation interaction at or near the edges of the detector surface. The shields can extend away from a holder of the detecting surface towards a radiation source or towards a center of the bore.

The detector segments can each include a holder that holds one or more semiconductor detectors. The holder can be made from a shielding material, such as tungsten. The holder can include an opening, and the one or more semiconductor detectors can be provided in the opening such that a continuous cathode of the one or more semiconductor detectors is on a first side of the holder, and a pixilated anode of the one or more semiconductor detectors can be provided on a second side of the holder that opposes the first side.

One of more of the detector segments can include a shield made of a radiation-shielding material to inhibit or block radiation from being incident on a side edge of the one or more semiconductor detectors. The shield can extend away from a holder of the detecting surface towards a radiation source or towards a center of the bore.

A side profile of the holder, with respect to the detector axis, can form a shape of a V or an upside-down V (or M, W, or upside-down M or W).

In the drawings, like reference numerals designate identical or corresponding parts throughout the several views. Further, as used herein, the words "a," "an" and the like generally carry a meaning of "one or more," unless stated otherwise.

Figure 2:
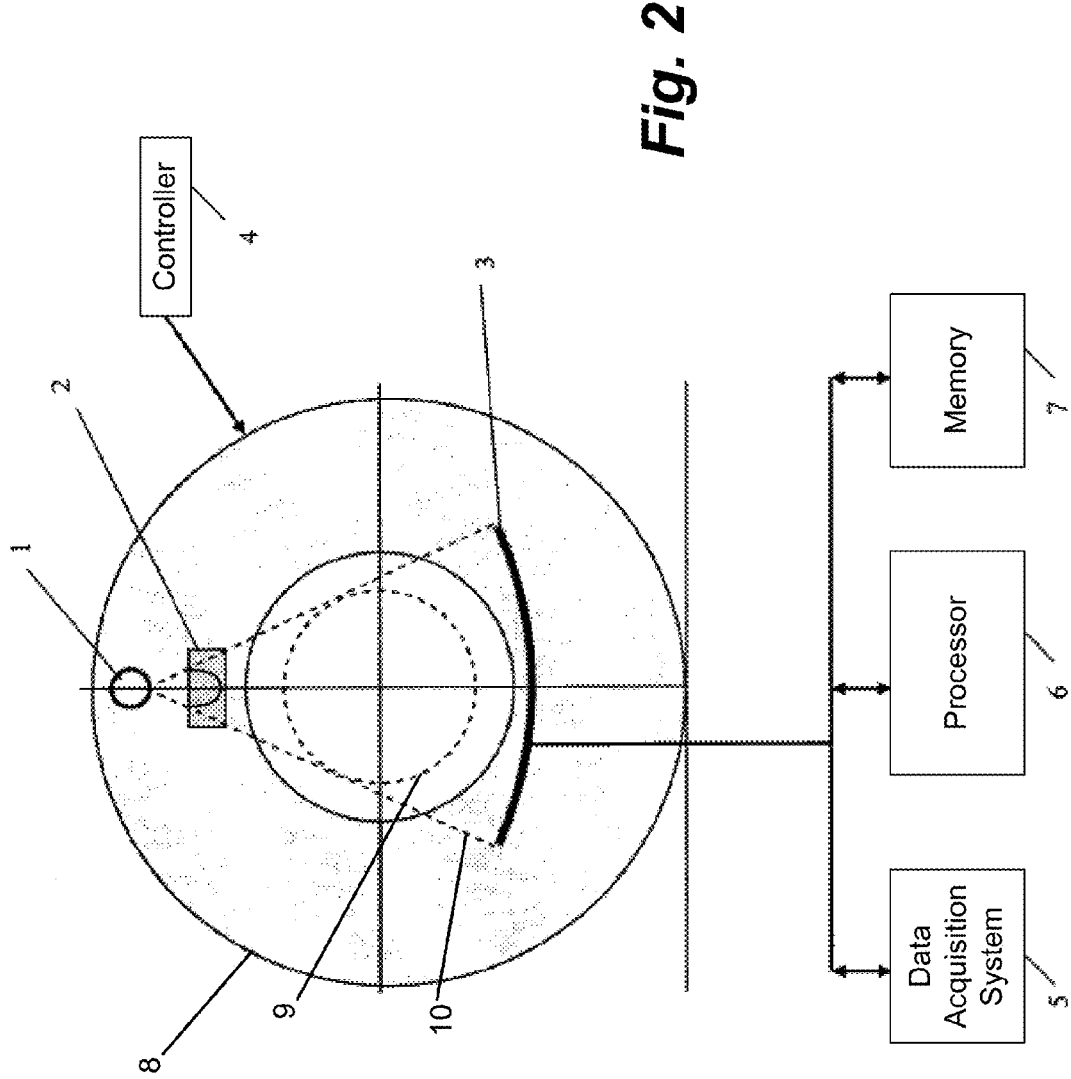
FIG. 2 is a schematic diagram of a mechanically simplified CT apparatus.

FIG. 2 illustrates a simplified schematic structure of a CT apparatus that can include a detector array that can detect photons. Aspects of this disclosure are not restricted to a CT apparatus as the medical imaging system. In particular, the structures and procedures described herein can be applied to other medical imaging systems, and the descriptions provided herein specifically relating to a CT apparatus and the detection of photons should be considered as exemplary.

A detector array, a photon detector and/or a photon detector array may be referred to herein merely as a detector. The CT apparatus illustrated in FIG. 2 includes an X-ray tube 1, filters and collimators 2, and a detector 3. The CT apparatus also includes additional mechanical and electrical components such as a gantry motor and a controller 4 to control the rotation of the gantry, control the X-ray tube 1, and control a patient bed. The CT apparatus also includes a data acquisition system 5 and a processor 6 to generate CT images based on the projection data acquired by the data acquisition system 5.

The processor 6 and data acquisition system 5 can make use of a memory 7, which is configured to store, e.g., data obtained from the detector 3 and reconstructed images.

The X-ray tube 1, filters and collimators 2, detector 3 and controller 4 can be provided in a frame 8 that includes a bore. The frame 8 has a general cylindrical or donut shape. In the view shown in FIG. 2, a longitudinal axis of the bore of the frame 8 is in the center of the bore, and extends into and out of the page. An interior of the bore, identified as area 9, is a target area for imaging. An object to be scanned, such as a patient, is placed in the target area with, e.g., a patient table. The object can then be irradiated by the X-ray tube 1 with a fan or cone of radiation 10, which generally, substantially or effectively cross-sects the object with respect to the longitudinal axis. The processor 6 is programmed to determine photon counts of captured incident X-ray photons.

In FIG. 2, the detector 3 is a rotational detector array that rotates with the X-ray tube 1 with respect to the longitudinal axis. As discussed below, but not shown in FIG. 2, a stationary detector array can also be included, thus providing a rotational detector array and a stationary detector array, together, in the frame 8.

Figure 3:
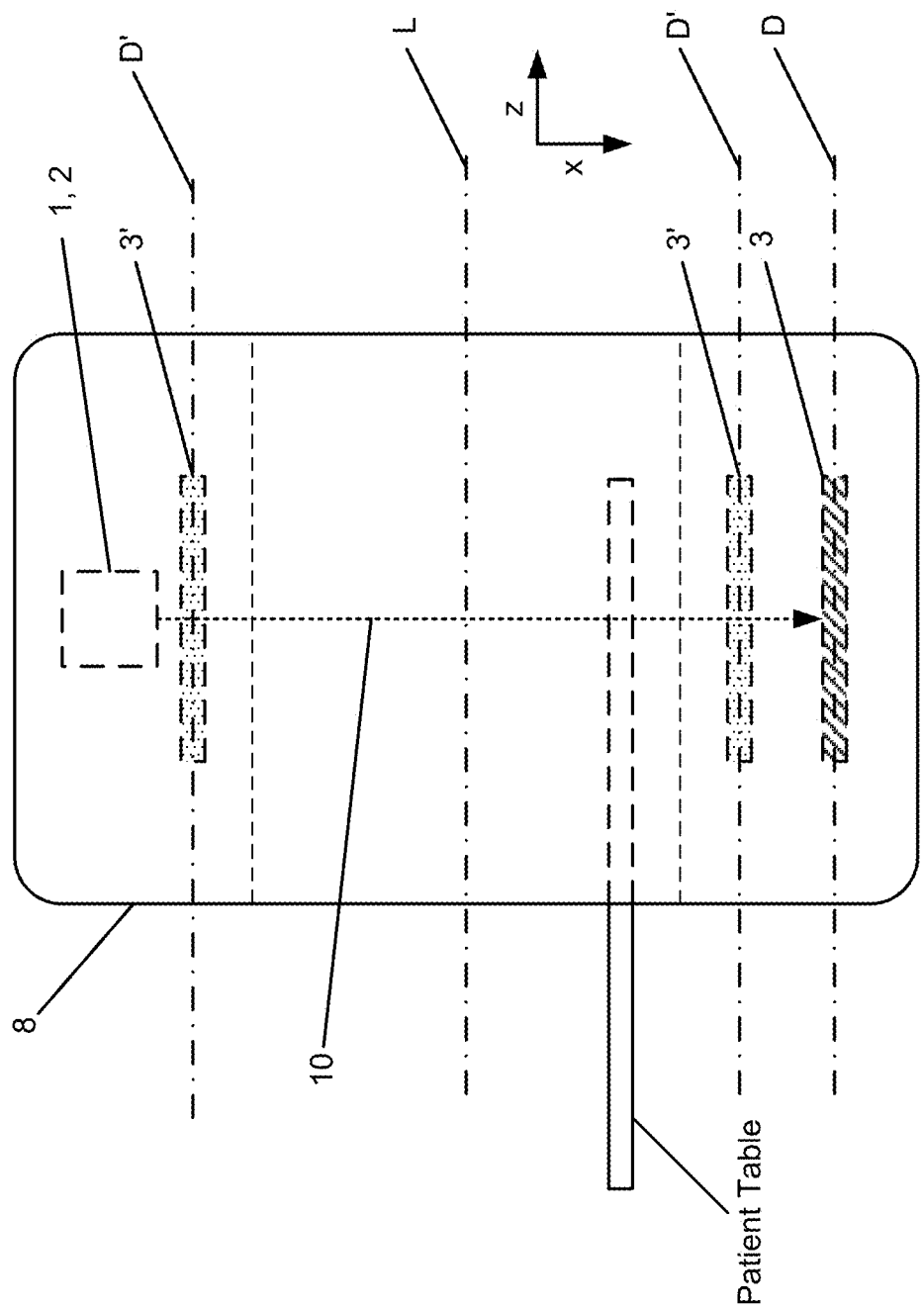
FIG. 3 is a schematic diagram of a mechanically simplified CT apparatus with a detector extending in a direction of a longitudinal axis.

FIG. 3 is a schematic diagram of a mechanically simplified CT apparatus with a detector arrays extending in a direction of a longitudinal axis. FIG. 3 is a side view of the CT apparatus shown in FIG. 2, illustrating a rotational detector array and a stationary detector array, together, in the frame 8. In particular, FIG. 2 is a view of a CT apparatus from the perspective of a longitudinal axis L, where this axis extends into and out of the page. In FIG. 3, the longitudinal axis L extends side-to-side across the page.

FIG. 3 illustrates a rotational detector array 3 as having a detector axis D as also extending side-to-side across the page. D is generally, substantially or effectively parallel to L. That is, the relationship between these two axes is parallel within a margin of a 2°, 1° or less. According to the various aspects described herein, a perfect geometrically "parallel" or "perpendicular" relationship is not generally necessary, and a "general, substantial or effective" relationship is suitable within a margin of 2°, 1° or less.

The rotational detector array 3 can rotate together with the X-ray tube 1 about the longitudinal axis L. A series of stationary detector arrays 3' can be provided, in a periodic or irregular fashion, around the frame 8, and can form a circular shape when viewed along the longitudinal axis L.

The series of stationary detector arrays 3' can be provided along respective detector axes D', which extend side-to-side across the page. D' is generally, substantially or effectively parallel to L and D. That is, the relationship between these axes is parallel within a margin of a 2°, 1° or less. According to the various aspects described herein, a perfect geometrically "parallel" or "perpendicular" relationship is not generally necessary, and a "general, substantial or effective" relationship is suitable within a margin of 2°, 1° or less.

FIG. 3 also illustrates a Patient Table extending into the bore of the frame 8, and the fan or cone 10. The fan or cone 10 has a major length in the side-to-side dimension in the view of FIG. 2, and a minor length in the side-to-side dimension in the view of FIG. 3. In exemplary implementations, the fan or cone 10 can impinge upon both of the rotational detector array 3 and one of the stationary detector arrays 3'. Further, although FIG. 3 illustrates the rotational detector array 3 and the stationary detector arrays 3' as having a common dimensional length in the z-direction, other implementations include varying lengths in the z-direction between the rotational detector array 3 and the stationary detector arrays 3' or amongst the stationary detector arrays 3'.

FIG. 4 illustrates a detector array 11 that has an incidence surface, with respect to an incoming beam 12 from an X-ray source, which is generally or approximately perpendicular to the beam 12. The incoming beam 12 can coincide with that illustrated as fan or cone 10 in FIG. 3.

As shown in FIG. 4, the detector array 11 extends in the z-direction, and the beam 12 propagates, generally, in the x-direction. The detector array 11 has dimensions d (a length in the x-direction) and p (a length in the z-direction). The x-direction can be considered a radial direction that extends from a point source, the X-ray source, where the fan or cone of radiation propagating from the X-ray source has a circular arc length along a common distance from the X-ray source. In comparison to a cylindrical coordinate system, the xdirection could be considered equivalent to r, where a bore of the CT machine extends in the z-direction, and a e direction defines an angular dimension that can coincide with an angular component of the fan or cone of radiation 10. The z-direction can also coincide with a longitudinal dimension of a patient, with reference to FIGS. 6-7, and a longitudinal axis of the bore.

Adverting back to FIG. 4, due to fanning of the beam 12, an actual perpendicular relationship will generally exist for a portion of the beam 12 and a portion of the detector array 11, and specifically for a point of a segment of the detector array 11 if that segment directly faces the X-ray source. This relationship can be described as providing a flat or planar detector with respect to a propagation direction of a beam, and can generally be referred to as providing a perpendicular relationship, even though a true 90° angle is not necessarily provided.

In FIG. 4, the detector array 11 is illustrated as having four channels 14, and the detector array 11 can be positioned along an arc length that coincides with the arc length of the detector 3 shown in FIG. 2 or in a direction that is transverse to the arc length of the detector 3 shown in FIG. 2. The shown four channels 14 may be referred to herein as pixels or individual detecting regions. In an exemplary implementation, a detector array can include eight channels or pixels, and is coupled to an eight-input ASIC, that accepts the output signals from the detector array. However, other combinations are possible.

FIG. 5 illustrates a detector array 16 that includes an exemplary eight channels 18. The detector array 16 is tilted, with respect to the x-direction, by an angle $\alpha$. As in the case with the illustration of detector array 11 in FIG. 4, the beam 12 propagates, generally, in the xdirection. With respect to the dimensions d and p of the detector array 11, the detector array 16 has dimensions d' and p'. In FIG. 5, the z-direction coincides with a detector axis and is parallel to a longitudinal axis of a bore of a medical imaging system, such as a CT apparatus.

In one implementation, in order for a tilted detector array to maintain a same thickness (which coincides with detection efficiency) and pitch (which coincides with spatial resolution) as that of a non-tilted detector, the following relationships are satisfied:

$$d' = d \sin \alpha \tag{1}$$

$$p' = p/\sin \alpha \tag{2}$$

In an exemplary implementation, the following relationship is satisfied:

$$4 < 1/\sin \alpha < 16, \text{which is } 3.6° < \alpha < 14.5° \tag{3}$$

However, particular implementations can vary the value of a based on experimental results and intended tasks to achieve an optimal value for $\alpha$.

In the exemplary implementations discussed herein, a width of a channel or pixel is not changed or affected with respect to conventional detectors or a non-tilted detector. However, the width of a channel or pixel in a tilted detector can be changed to be made larger or smaller than that of conventional detectors or a non-tilted detector. In some aspects, then, a tilted detector, in comparison to a non-tilted detector, can provide for more pixels or channels per arc of a fan or cone of X-rays, where the arc and pixels between the tilted detector and the non-tilted detector otherwise have the same dimensions. However, as schematically illustrated in FIG. 5, as compared to FIG. 4, twice the number of channels/pixels is provided in the z-direction by the tilted detector. In another implementation, a same amount of channels/pixels in the z-direction can be provided (between a non-tilted detector and a tilted detector) by increasing a width of the channels for the tilted detector.

Further, although the exemplary schematic comparison between FIGS. 4 and 5 illustrates that the tilted detector has a same thickness (dimension d') as that of the thickness of the non-tilted detector, the thickness of the tilted detector can be made smaller than that of the non-tilted detector, while still providing a same amount of detector material (in the x-direction) for the X-ray to interact with, in accordance the above relationships (1) and (2).

The detector array 16 can also output signals using multiple circuits or circuit channels to reduce data transmission/processing load on the respective circuits.

In one implementation, only stationary detector arrays have tilted segments, whereas a rotational detector array is not tilted. The rotational detector array can have a curved surface that curves with respect to a fan or cone of a radiation source.

Figure 6:
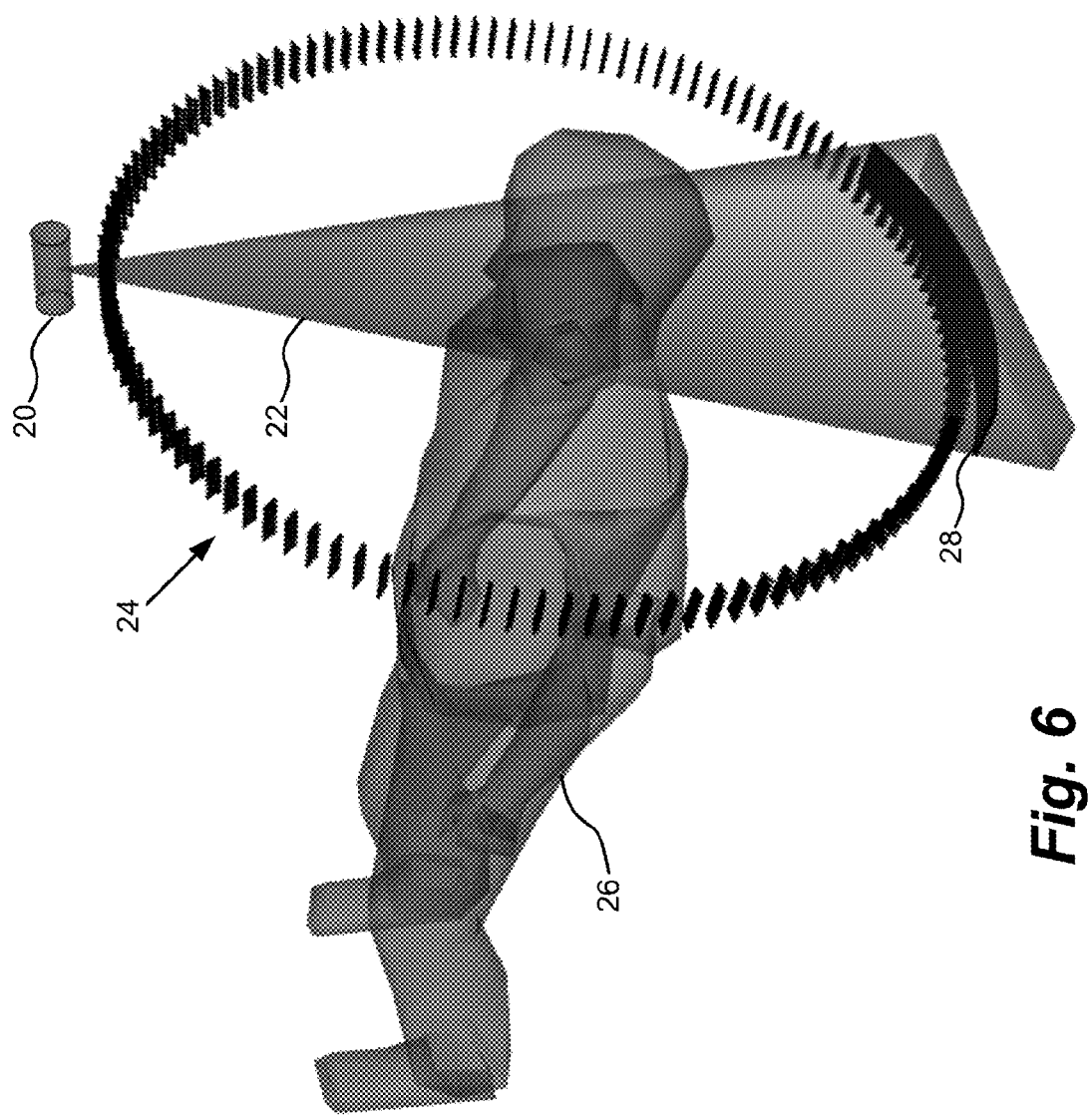
FIG. 6 is an illustration of a simplified CT apparatus scanning a patient with an X-ray source in one implementation.
Figure 7:
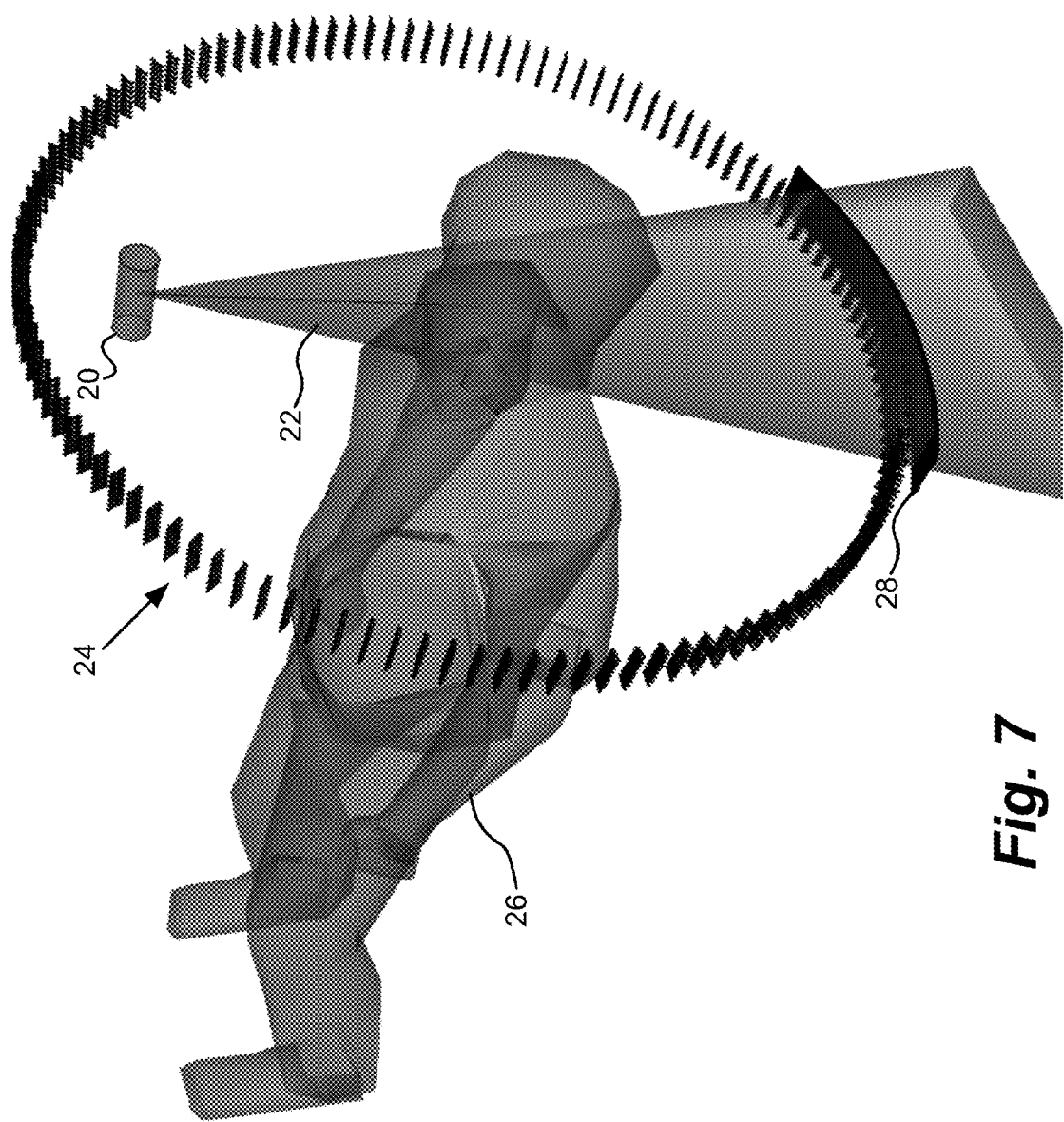
FIG. 7 is an illustration of a simplified CT apparatus scanning a patient with an X-ray source in another implementation.

FIGS. 6 and 7 illustrate exemplary simplified CT assemblies that include an X-ray source 20 that generates a fan or cone (beam) 22 of X-rays, a plurality of detector arrays 24 provided in a circular shape about a scanning area (which in these figures includes a patient 20 26 as an object to be scanned), and a detector array 28. Although not shown, a collimator can also be provided. The detector array 28 can be a rotational detector array that rotates with the X-ray source 20, whereas the detector arrays 24 can be stationary detector arrays with respect to the X-ray source 20.

In FIGS. 6 and 7, the detector arrays 24 are not arranged in a curve that coincides with a curve of fan or cone 22 due to a difference in radial origins. That is, the fan or cone originates from a point that is close to a circumference of the circular shape formed by the detector arrays 24, whereas the circular shape formed by the detector arrays 24 can be defined by an origin at a center of the scanning area (where the target/patient is provided). In another implementation, the detector arrays 24 can be provided in a curve that coincides with a curve of the fan or cone 22 such that a distance between discrete detector arrays 24 is the same as measured from the X-ray source 20. Here, the detector arrays 24 and the X-ray source 20 can be provided with rotational assemblies that rotate the detector arrays 24 and the X-ray source 20 together around the scanning area.

Otherwise, in the implementation illustrated in FIGS. 6 and 7, the detectors arrays 24 can be maintained as stationary, while the X-ray source 20 and the detector array 28 are provided to rotate around the scanning area by, e.g., a guide track and a computer-controlled motor.

Further, although the implementations shown in FIGS. 6 and 7 illustrate the detectors arrays 24 as forming a complete circle around a target area, other implementations include only providing the detector arrays 24 around a part of the circle, such as a part that only coincides with the fan or cone 22. Here, the detector arrays 24 can be rotated together with the radiation source 20.

In FIG. 6, the X-ray source 20 is provided outside the circular shape of the detector arrays 24. In FIG. 7, the X-ray source 20 is provided inside the circular shape of the plurality of detector arrays 24.

The CT assemblies described herein can be in accordance with a sparse $4^{th}$ generation CT geometry and structure or a $3^{rd}$ generation CT geometry structure. That is, the detector structures and associated features described herein are not limited to a particular CT or other medical imaging geometry, structure, or technology.

Figure 8:
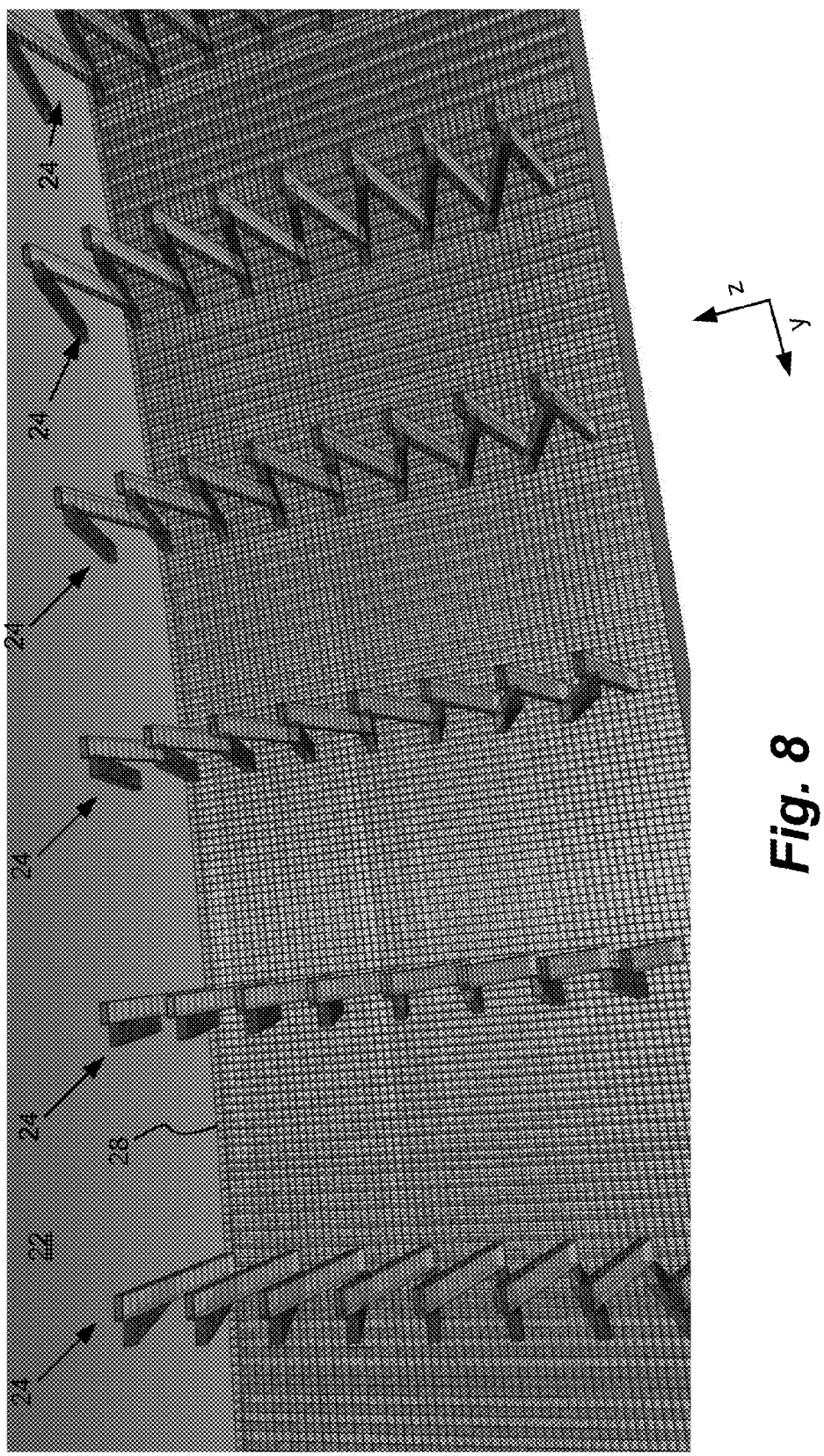
FIG. 8 is an enlarged view of detectors of the simplified CT apparatus of FIG. 6 or FIG. 7.

FIG. 8 is an enlarged view of six of the detector arrays 24 in a region of the fan or cone 22. The detector arrays 24 each extend in respective detector axes that extend in the z-direction, and each have an alignment direction that faces, in a radial direction, a center of the circular shape of the detector arrays 24 (a longitudinal axis), so that the detector arrays 24 in the region of the fan or cone 22 generally face (but are not directly pointed at) the X-ray source 20. Stated differently, each of the detector arrays 24 can generally coincide with a trajectory of the fan or cone 22, but one or none of the detector arrays 24 may be aligned so as to be perpendicular to (i.e., point directly at) the X-ray source 20.

On the other hand, with respect to a pointing direction of the detector arrays 24 residing in an x-z plane, where x-axes coincide with radial directions extending from a center of the circular shape of the detector arrays 24, and z-axes are parallel to a longitudinal direction of a barrel of the CT assembly, individual detector arrays 24 may be provided with a discrete motor and tilting mechanism to tilt the individual detector arrays 24 with respect to the x-z plane. This tilting (as opposed to the tilting illustrated in FIG. 5) can change the pointing direction of an individual detector array 24 from the center of the circular shape formed by the detector arrays 24 to the X-ray source 20. In other words, the detector arrays 24 can be adaptively and automatically pointed towards the X-ray source 20 based on a position of the X-ray source 20. The exemplary implementations shown in the drawings, however, merely show the various detectors, arrays and segments in a stationary configuration, without active tilting mechanisms, for simplicity.

FIG. 8 illustrates an exemplary implementation of the detector arrays 24 in that individual segments thereof are in a staggered or off-set alignment, where commonly angled segments (i.e., a first set) thereof share a common alignment in the z-direction, where adjacent detector arrays 24 (i.e., a second set) are displaced from each other in the y-direction (a circumferential direction with respect to the circular shape formed by the detector arrays 24), and where adjacent segments of a particular detector array 24 stagger, with respect to in the y-direction, as the particular detector array 24 extends in the z-direction. In other words, the first and second sets are staggered so as to be offset and provided on separate sides of a detector axis that is parallel to a longitudinal axis.

In an exemplary implementation, the commonly angled segments form a continuous or substantially continuous detection region with respect to the z-direction. That is, as a first angled segment terminates, a next second angled segment begins, where the termination point of the first angled segment coincides with or substantially coincides with the beginning point of the second angled segment with respect to the z-direction. In the x-direction, the termination point of the first angled segment is displaced with respect to the beginning point of the second angled segment, and the displacement has a magnitude corresponding to the projection of the segments in the x-direction.

Figure 9:
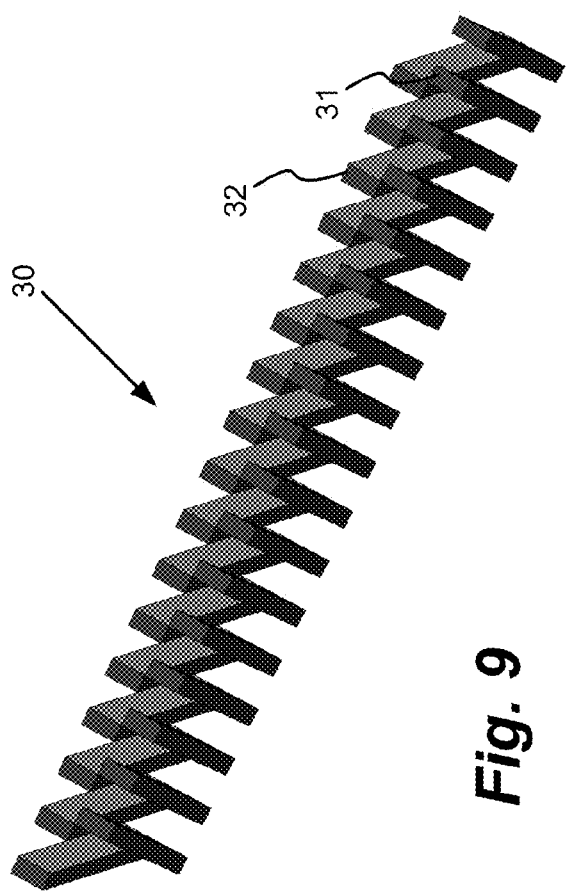
FIGS. 9-10 illustrate exemplary implementations of staggered or off-set tilted detectors.
Figure 10:
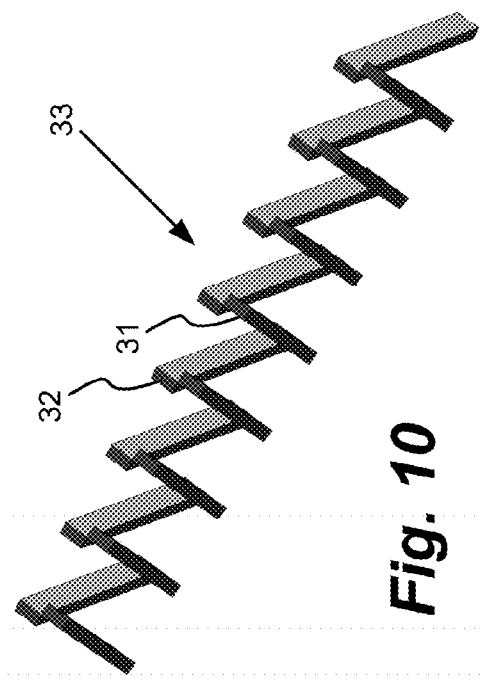

FIGS. 9-10 illustrate exemplary implementations of detector arrays. In FIG. 9, a detector array 30 is illustrated. The detector array 30 has staggered segments 31 and 32. Segments 31 are provided on one side of the detector array 30, whereas segments 32 are provided on another side of the detector array 30. These segments 31 and 32 are alternately provided with opposing angles α with respect to an x-direction (a radial direction extending to a center of the circular shape formed by a plurality of the detector arrays arranged in a circle around a target scanning area).

In the exemplary implementation shown in FIG. 9, the angle α is 7°, such that the segments 31 and 32 are alternately provided with opposing angles of +7° and −7°, with respect to the x-direction. The opposing angles can be referred to as opposing reflective angles or the like due to their reflective-like alignment with respect to the x-direction. The segments 31 and 32 are also provided in a staggered arrangement such that the segments are side-by-side, form apexes at an intersection of detecting surfaces at a top end, and form apexes at an intersection of detecting surfaces at a bottom end. Alternatively, the top and bottom ends can include apexes formed by an intersection of a non-detecting surface, such as a holder, shield or substrate for a material forming a detecting surface. Various combinations of alignments of the apexes can be implemented.

In FIG. 10, a detector array 33 is illustrated. The detector array 33 has staggered segments 31 and 32 that can be the same as those relating to the detector array 30 of FIG. 9. However, the segments 31 and 32 for the detector array 33 are alternately provided with opposing angles of +14° and −14°, with respect to an x-direction. The angle α can be varied based on a particular implementation, in the range of 0° to +/−90°.

In these exemplary implementations, the detector arrays can have a periodic repeating structure that extends for a predefined length in the z-direction. In FIGS. 9-10, a period is defined as two adjacent segments 31 and 32 of opposing reflective angles. However, other periods can be defined of varying angles or stagger alignments (including a non-stagger alignment).

Figure 11:
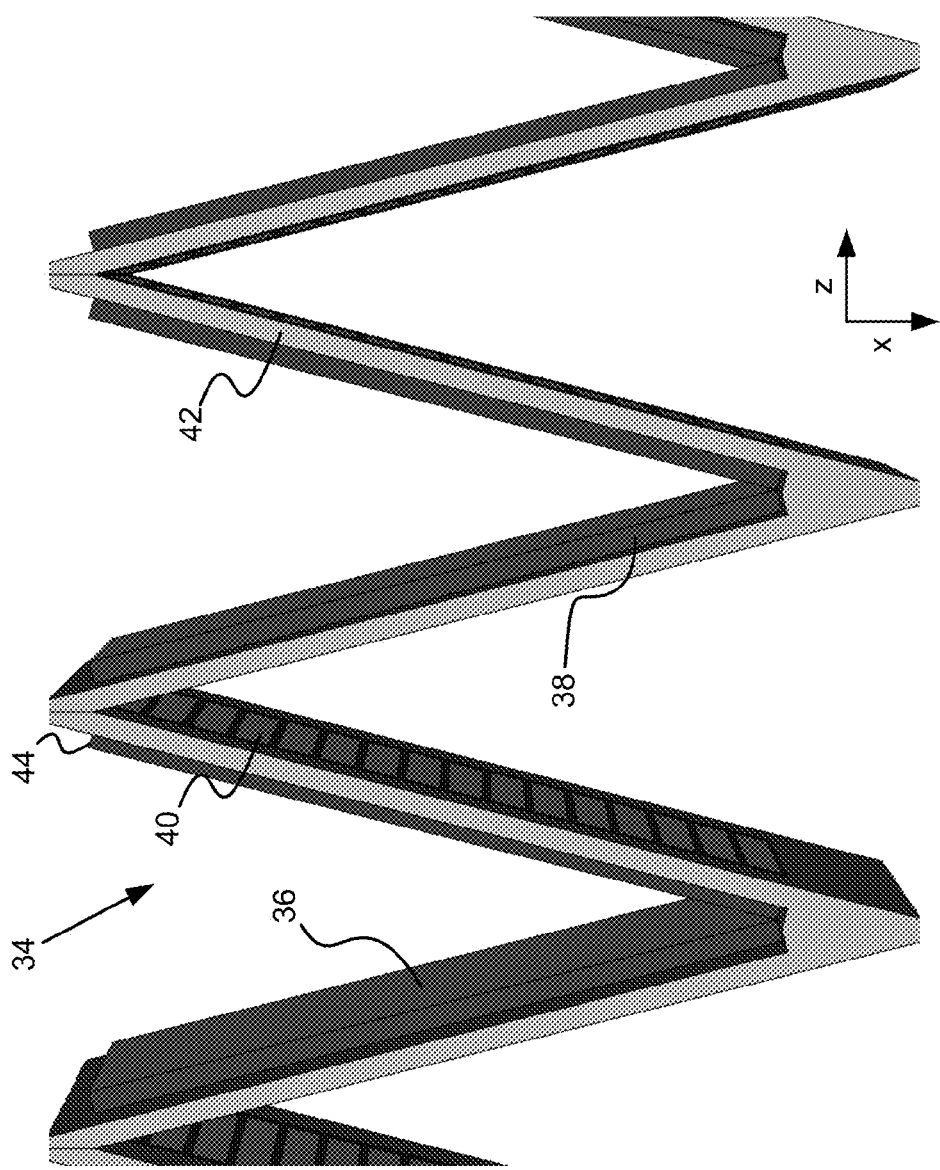

FIG. 11 illustrates a non-staggered tilted detector array 34. The non-staggered tilted detector array 34 includes a plurality of segments that form a V, W, or M shape period that is repeated for a predefined length in the z-direction when viewed from the side (as in the view of FIG. 11). Each segment includes a detecting surface 36 of a detector material 38. In exemplary implementations, the detecting surface 36 is a detector electrode that is a continuous cathode. On the opposing side of the detector material 38, a pixilated anode 40 can be provided. The pixilated anode 40 can include a plurality of pixels or channels, including 4-16, 24, 32, or more according to an electronic signal processing design. Each pixilated anode 40 (or a portion of the pixels or channels thereof) can be coupled to a discrete processing unit (or a discrete input thereof), such as an ASIC and/or an analog-to-digital converter for coupling to a processing system. Further, the general structure of a segment as illustrated in FIG. 11 can be utilized with the other exemplary implementations described herein.

Figure 12:
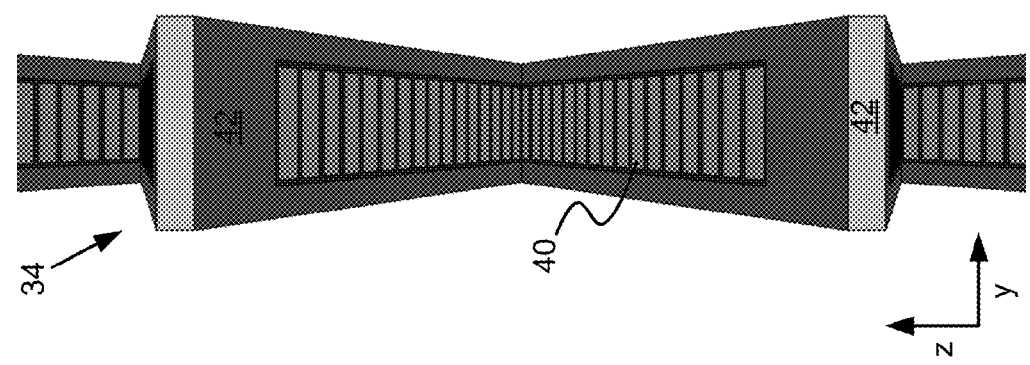
FIGS. 11-13 illustrate various views of an exemplary implementation of a non-staggered tilted detector.

FIG. 11 also illustrates a holder 42. The holder 42 can consist of or include shielding materials that generally block radiation, and can provide a holding structure for holding the materials and components of the detector in alignment among the various segments. The materials can be specifically selected to block photons (i.e. non-X-ray photons), X-rays (X-ray photons), or both photons and X-rays. An exemplary material for the holder 42 is tungsten. In another implementation, the holder 42 is not made from a shielding material. FIG. 12 illustrates an x-direction "bottom to top" view of the non-staggered tilted detector array 34, and illustrates the holder 42 encompassing a plurality of the pixels of the pixilated anode 40.

In FIGS. 11 and 12, the holder 42 is flush an exterior surface of the pixels of the pixilated anode 40, and the detecting surface 36 protrudes away from the holder 42. Alternatively, the holder 42 can be provided so as to recess one, both or none of the pixels of the pixilated anode 40 and the detecting surface 36. Additionally, the holder 42 can be provided so as to have respective surfaces that are flush with one, both or none of the pixels of the pixilated anode 40 and the detecting surface 36. When the holder 42 includes a shielding property, flush or recess mounting of the pixilated anode 40 and the detecting surface 36 can inhibit radiation interaction with undesirable portions of the pixilated anode 40 or a side surface of the detector material 38, which can improve energy resolution and/or separation.

Figure 13:
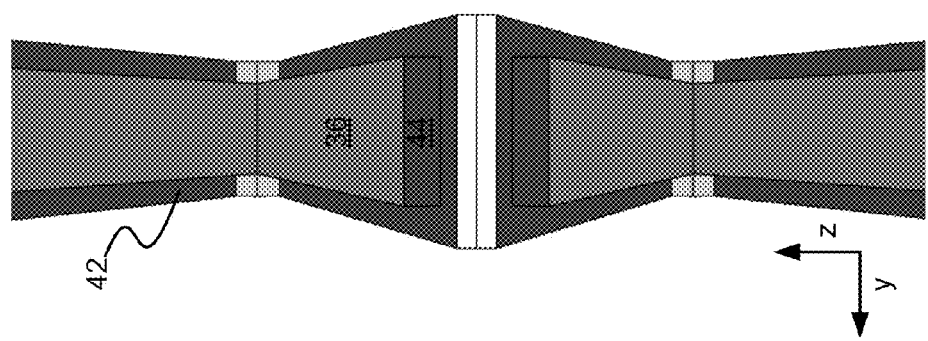

As shown in FIGS. 11 and 13 (FIG. 13 being an x-direction "top to bottom" view of the detector array 34), the top ends of the detecting surfaces of each segment have side surfaces 44 that are subject to X-rays. To inhibit X-ray interaction with the side surfaces, shielding material (e.g., by a holder) can be added to inhibit an X-ray from interacting with a detector via a side surface. Shields can also be provided, either in combination or separately.

Figure 15:
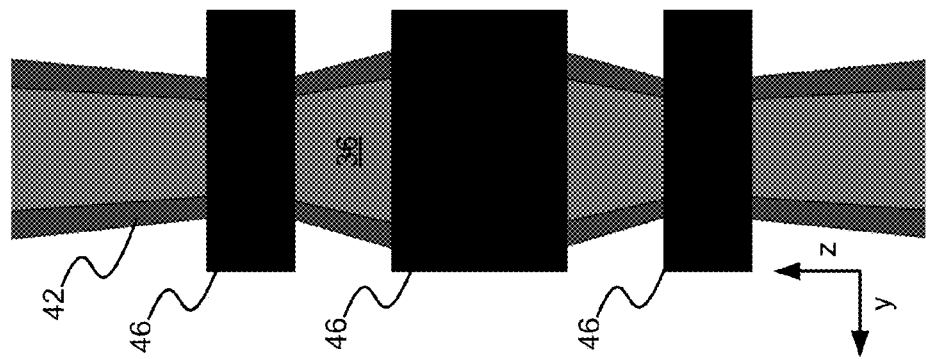
FIGS. 14-15 illustrate the exemplary implementation shown in FIGS. 11-13 further including shields.
Figure 14:
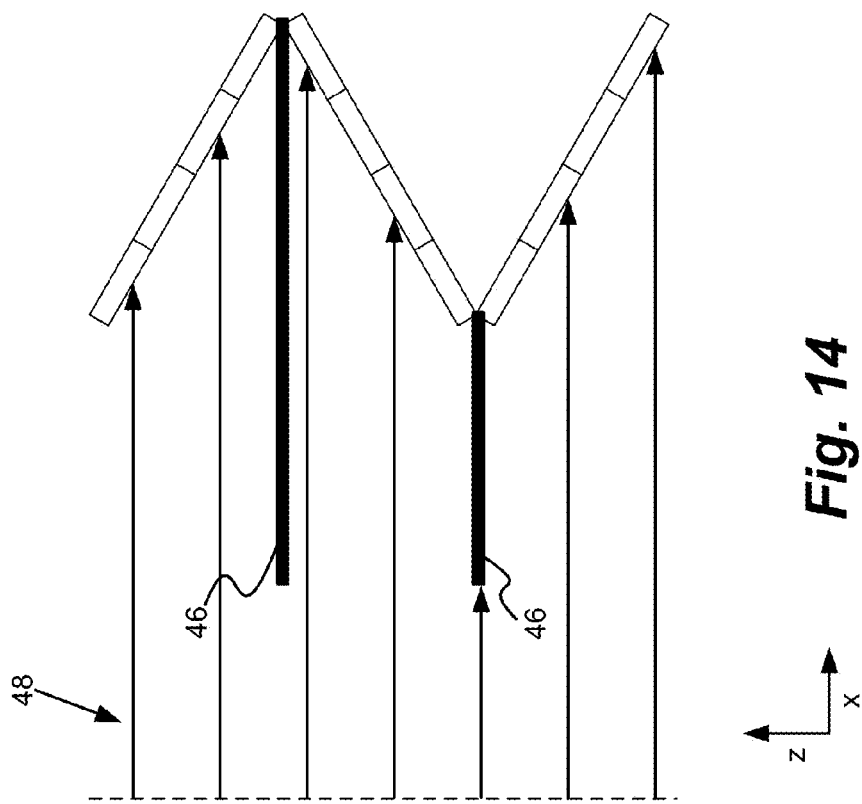

As schematically illustrated in FIGS. 14-15, shields 46 that include a shielding material, such as tungsten, can be utilized at points of intersection between segments. The shields 46 can be provided at both of or one of top apexes and bottom apexes of the segments of the implementation shown in FIGS. 14-15 or the other exemplary implementations described herein.

The shields 46 can be relatively short caps or covers that do not have a very large dimension in the x-direction. In another implementation, as illustrated in FIGS. 14-15, the shields 46 can have a significant dimension in the x-direction so as to limit a number of X-rays of a fan or cone 48 that are incident on a neighboring segment, or that reflect (or are otherwise unintentionally generated by scattering or other method) from one segment to a neighboring segment, to improve resolution. The shields 46 and the arrangement of the segments (i.e., the detecting surfaces 36) as shown in FIGS. 14-15 can also be arranged so as to provide for dead zones in which a portion of the detector in the z-direction is ineffective. These dead zones can coincide with the shields 46. The dimension in the z-direction and/or the x-direction of the shields 46 can be varied between top and bottom apexes or based on a relative position along the detector array in the z-direction.

In FIG. 14, a relatively longer shield 46 provided at a bottom apex can prevent secondary photons from escaping one detector surface to hit an opposing detector surface. This can reduce cross-talk. A relatively shorter shield 46 provided at a top apex can block a primary beam from radiating an anode region of a detector/segment. This can improve energy separation and resolution.

Adverting back to, e.g., FIGS. 8-10, off-set or staggered segments can be provided, where each side of a detector array is a rotation, in the x-direction, by 180°. Alternatively stated, the segments alternate between +α and −α angular tilts every segment.

Figure 16:
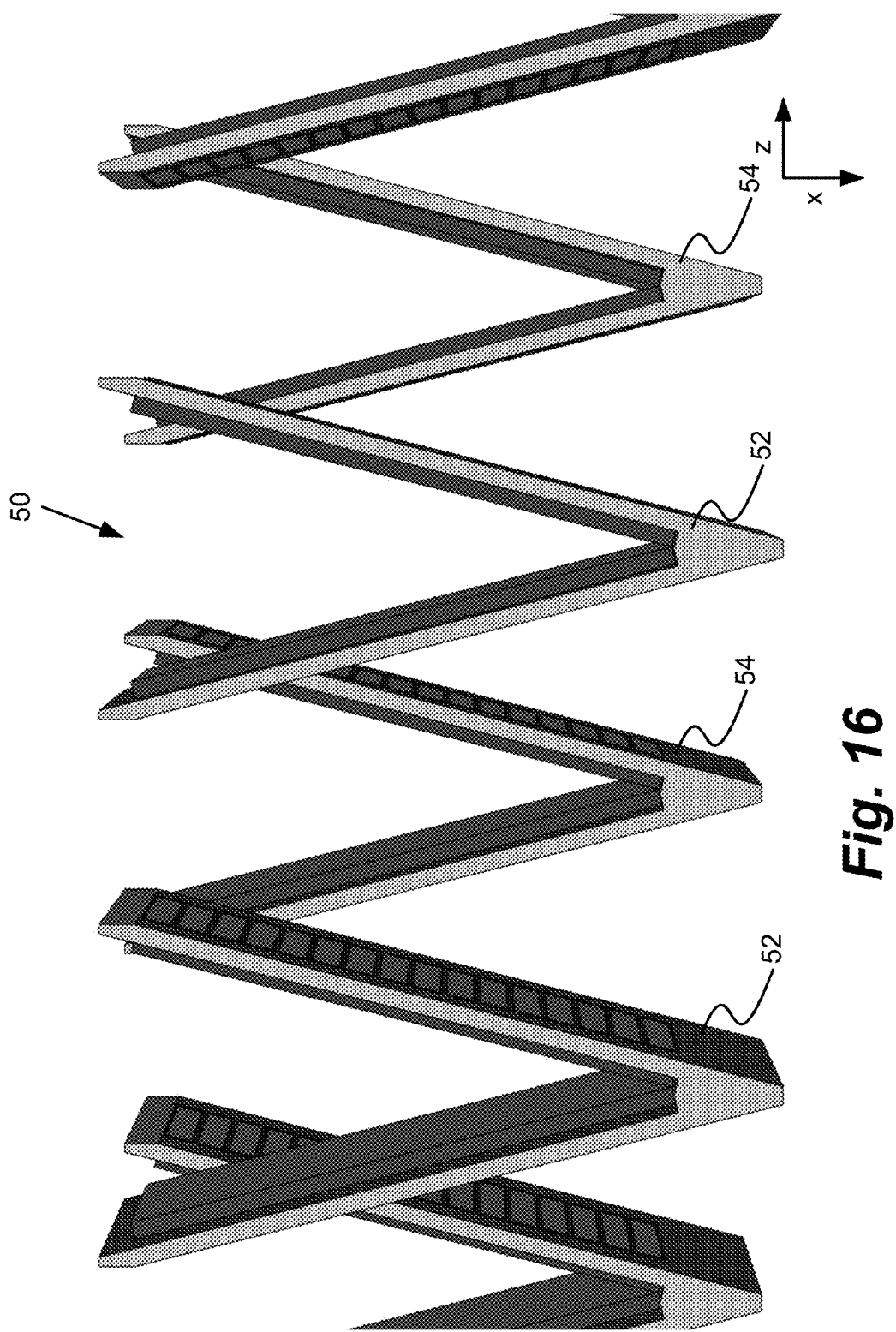

In another implementation, as illustrated in FIG. 16, a detector array 50 can include segments that form a V shape. Although not shown, the segments can also form a W, M or upside-down V shape. In the exemplary implementation shown in FIG. 16, the V-shaped segments are staggered. In the perspective of FIG. 16, foreground segments 52 are off-set in the y-direction with respect to background segments 54. The segments 52 and 54 are aligned such that the detecting surfaces provided thereon intersect with respect to a line in the y-direction. FIGS. 17-18 illustrate respective top (in the +x-direction) and bottom (in the −x-direction) views of the detector array 50. Aspects of the other discussed exemplary implementations can otherwise be combined with the exemplary structures illustrated in FIG. 16-18.

Although not restricted to a particular type of detector, exemplary detectors include semiconductor-based detectors that include a detector material of CZT (cadmium zinc telluride—CdZnTe) or CdTe (cadmium telluride). Further, an exemplary implementation of this disclosure involves a spectral CT with sparse CZT detectors.

Exemplary implementations of a CZT detector array can include a CZT thickness of 1 mm. With an exemplary angle α of 20°, a nominal thickness of the detector is approximately 2.9 mm in the x-direction (the beam direction of the incident X-ray beam/fan/cone). This is a sufficient thickness to stop X-ray photons. However, other dimensions or angles can be utilized.

In an implementation to make a detector of a multi-slice CT compact, a detector array can be divided into several pieces, which are tilted in different directions, which may be off-set in the y-direction. Leading and tailing edges of adjacent or neighboring detectors or segments thereof can coincide in the x-direction, or they can be off-set.

Blockers or shields can be included to stop escaped photons and electrons. These can be provided at joint edges that face the X-ray source, and can shield an anode side of the detector to improve energy resolution.

A rotating detector according to the exemplary implementations discussed herein can be an energy integrating detector that does not and cannot measure spectral information. The stationary (tilted) detector arrays can be photon counting detectors (PCDs) (e.g., CZT or CdTe based detectors) that can generate spectral information. The PCDs can be sparsely distributed in a circle inside the rotation circle (i.e., the frame) of the CT apparatus. Since a maximum count rate of the PCDs may not meet a predetermined requirement (e.g., $10^8$ cps/$mm^2$ of current CT systems), the PCDs are tilted in accordance with the disclosures provided herein to achieve a desired count rate.

By tilting the detector relative to an incident X-ray beam, energy resolution can be improved by reducing the range of the depth of charge generation. The counting rate can be increased because of the geometric factor and a thinner detector (e.g., a thinner amount of CZT compared to a non-tilted detector). A thinner CZT reduces charge collecting time. In addition, a thinner CZT has less charge sharing and leads to better spatial resolution.

In additional to improving count rate performance and energy resolution, a tilted detector design in accordance with the exemplary implementations discussed herein can reduce the effect of the following phenomena and simplify the corrections thereof by a processor or processing system.

(1) Ballistic Deficit

A thinner detector material (e.g., CZT) will have shorter time of flight with reduced ballistic deficit. Since the interaction of photons and CZT is near the surface (i.e. the incident surface), a variation of time of flight is smaller, which can lead to a simpler correction method.

(2) Charge Sharing

Since the time of flight is shorter, the diffusion of charge is smaller. Consequently, charge sharing is reduced.

(3) Space Charge

Space charge due to hole trapping will occur close to the cathode and the drift time of the electrode between the space charge region will be shorter.

(4) K-Escape

Side K-escape is reduced and the crosstalk is improved. Back K-escape (toward the cathode) will increase and the correction is easier.

(5) Pileup

When time of flight is shorter, with shorter peaking time, detector dead time decreases and pileup decreases. Since the variation of time of flight is reduced, a simple, constant dead time can be used for pileup correction.

Figure 19:
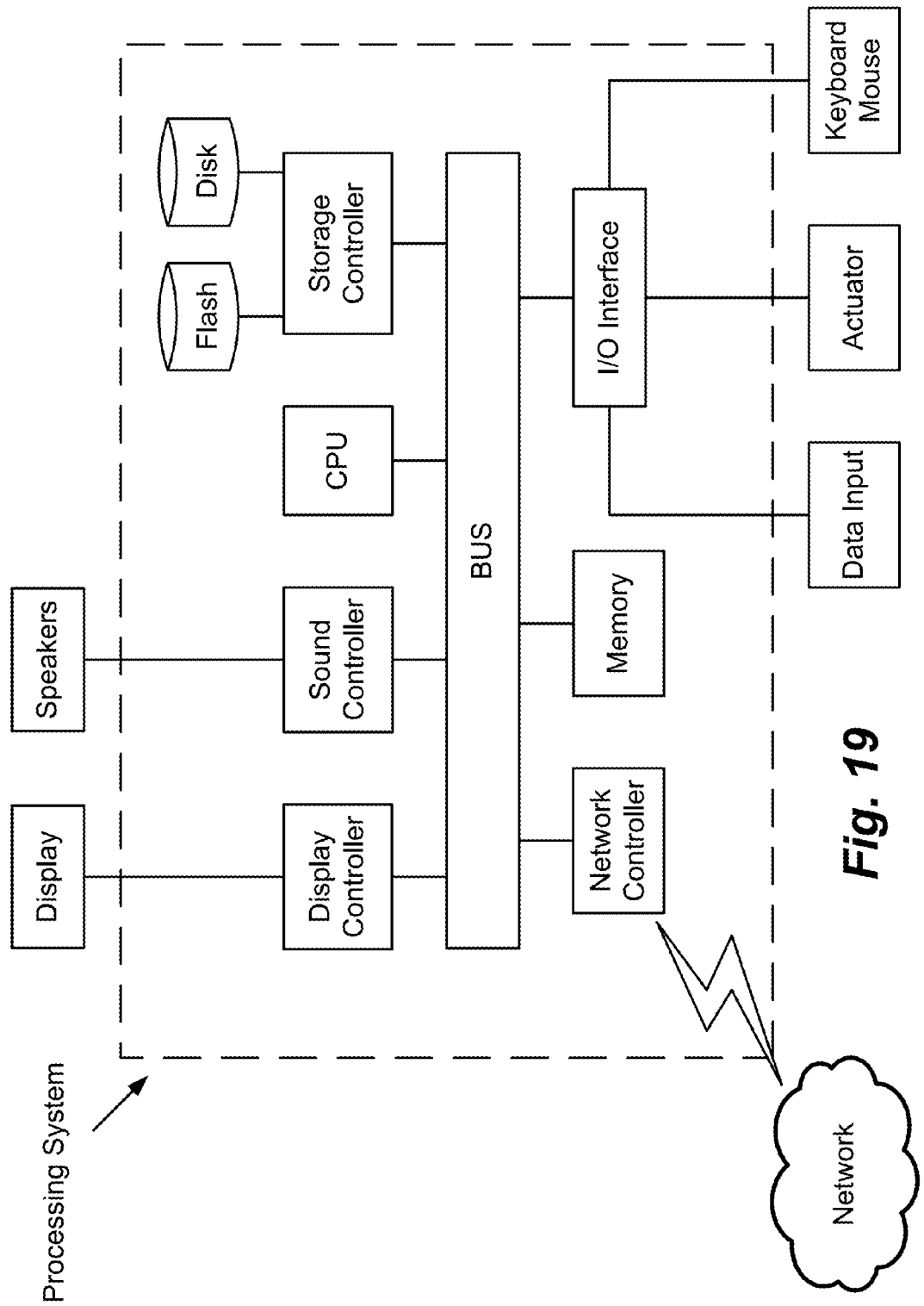
FIG. 19 is a schematic diagram of an exemplary processing system.

With reference to the structures illustrated in FIG. 2, an exemplary processing system is illustrated in FIG. 19. This exemplary processing system can be implemented using one or more microprocessors or the equivalent, such as a central processing unit (CPU) and/or at least one application specific processor ASP (not shown). The microprocessor is a circuit that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure. Other storage mediums can be controlled via a controller, such as a disk controller, which can controls a hard disk drive or optical disk drive.

The microprocessor or aspects thereof, in alternate implementations, can include or exclusively include a logic device for augmenting or fully implementing this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU. One or more processors in a multi-processing arrangement may also be employed to execute sequences of instructions contained in memory. Alternatively, hard-wired circuitry may be used in place of or in combination with software instructions. Thus, the exemplary implementations discussed herein are not limited to any specific combination of hardware circuitry and software.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output) interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes or algorithms of this disclosure can be connected to the I/O interface to provide additional functionality and configuration options, or control display characteristics. Moreover, the monitor can be provided with a touch-sensitive interface for providing a command/instruction interface.

The above-noted components can be coupled to a network, such as the Internet or a local intranet, via a network interface for the transmission or reception of data, including controllable parameters. A central BUS is provided to connect the above hardware components together and provides at least one path for digital communication there between.

The data acquisition system 5, the processor 6 and the memory 7 of FIG. 2 can be implemented utilizing one or more processing systems in accordance with the exemplary implementation shown in FIG. 19. In particular, one or more circuits or computer hardware units coinciding with one or more of the devices illustrated in FIG. 19 can provide for the functions of the data acquisition system 5, the processor 6 and the memory 7. Further, the processing systems, in one implementation, can be connected to each other by a network or other data communication connection. One or more of the processing systems can be connected to corresponding actuators to actuate and control movement of the gantry, the X-ray source, and/or the patient bed.

Suitable software can be tangibly stored on a computer readable medium of a processing system, including the memory and storage devices. Other examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. The software may include, but is not limited to, device drivers, operating systems, development tools, applications software, and/or a graphical user interface.

Computer code elements on the above-noted medium may be any interpretable or executable code mechanism, including but not limited to scripts, interpretable programs, dynamic link libraries (DLLs), Java classes and complete executable programs. Moreover, parts of the processing of aspects of this disclosure may be distributed for better performance, reliability and/or cost.

The Data Input portion of the processing system accepts input signals from a detector or an array of detectors by, e.g., respective wired connections. A plurality of ASICs or other data processing components can be provided as forming the Data Input portion, or as providing input(s) to the Data Input portion. The ASICs can receive signals from, respectively, discrete detector arrays or segments (discrete portions) thereof. When an output signal from a detector is an analog signal, a filter circuit can be provided, together with an analog-to-digital converter for data recording and processing uses. Filtering can also be provided by digital filtering, without a discrete filter circuit for an analog signal. Alternatively, when the detector outputs a digital signal, digital filtering and/or data processing can be performed directly from the output of the detector.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover such forms or modifications as would fall within the scope and spirit of this disclosure.

The invention claimed is:

1. A medical imaging system, comprising:
   a frame that has a bore that has a central longitudinal axis that intersects a target area for imaging;
   a radiation source to emit a fan or cone of emitted radiation in radial directions towards the target area so as to irradiate a cross-section of the target area with respect to the central longitudinal axis; and
   a detector array including a plurality of detector segments that extend along a detector axis that extends in a direction that is substantially parallel to the central longitudinal axis, the plurality of detector segments being arranged such that the fan or cone of radiation emitted from the radiation source passes through the target area and is incident on one or more of the plurality of detector segments, wherein
   each detector segment of the detector array includes a detecting surface that is tilted such that the detecting surface has a tilt with respect to the detector axis.

2. The medical imaging system of claim 1, wherein pairs of adjacent detector segments of the detector array have a side profile with a shape of a V or an upside-down V.

3. The medical imaging system of claim 2, wherein each of the pairs of adjacent detector segments includes:
   a first detector segment that has a first detecting surface with a first tilt with respect to the detector axis; and
   a second detector segment that has a second detecting surface with a second tilt with respect to the detector axis.

4. The medical imaging system of claim 3, wherein:
   the first and second detector segments of each of the pairs of adjacent detector segments of the detector array are joined to form an apex, with the first and second detector segments extending away from the apex;
   the first and second detecting surfaces are respectively tilted by tilt angles of $+\alpha$ and $-\alpha$ with respect to a perpendicular line that intersects the apex and extends between the central longitudinal axis to the detector axis; and
   $0°<\alpha<90°$.

5. The medical imaging system of claim 1, wherein the plurality of detector segments are staggered with respect to the detector axis, such that the plurality of detector segments comprises first and second sets of detector segments, respectively, on opposing first and second sides of the detector axis.

6. The medical imaging system of claim 5, wherein:
   first detecting surfaces of the first set of the detector segments have a common first tilt with respect to the detector axis; and
   second detecting surfaces of the second set of the detector segments have a common second tilt with respect to the detector axis.

7. The medical imaging system of claim 6, wherein a side profile of a detector segment of the first set of the detector segments and an adjacent detector segment of the second set of the detector segments has a shape of a V or an upside-down V.

8. The medical imaging system of claim 7, wherein:
   the side profile forms an apex, with adjacent detector segments extending away from the apex;
   detecting surfaces of the adjacent detector segments are respectively tilted by tilt angles of $+\alpha$ and $-\alpha$ with respect to a perpendicular line that intersects the apex and extends between the central longitudinal axis to the detector axis; and
   $0°<\alpha<90°$.

9. The medical imaging system of claim 5, wherein:
   a side-profile of detector segment pairs of the first set forms a shape of a V or an upside-down V; and
   a side-profile of detector segment pairs of the second set also forms the shape.

10. The medical imaging system of claim 9, wherein:
    the side profile of the detector segments pairs of the first and second sets forms an apex, with adjacent detector segments extending away from the apex;
    detecting surfaces of the adjacent detector segments are respectively tilted by tilt angles of $+\alpha$ and $-\alpha$ with respect to a perpendicular line that intersects the apex and extends between the central longitudinal axis to the detector axis; and
    $0°<\alpha<90°$.

11. The medical imaging system of claim 1, wherein:
each of the plurality of detector segments includes a holder that holds one or more semiconductor detectors;
the holder includes an opening; and
the one or more semiconductor detectors are provided in the opening such that a continuous cathode of the one or more semiconductor detectors is on a first side of the holder, and a pixilated anode of the one or more semiconductor detectors is on a second side of the holder that opposes the first side.

12. The medical imaging system of claim 11, wherein one or more of the plurality of detector segments includes a shield made of a radiation-shielding material that extends away from the holder towards the radiation source to inhibit or block primary radiation from radiating an anode region including said pixilated anode or to inhibit or block secondary radiation from escaping the detector segment and encountering another detector segment.

13. The medical imaging system of claim 11, wherein a side profile of the holder, with respect to the detector axis, forms a shape of a V or an upside-down V.

14. The medical imaging system of claim 11, wherein the holder includes a radiation-shielding material to inhibit or block incident radiation from the radiation source.

15. A medical imaging system, comprising:
a frame that has a bore that has a central longitudinal axis that intersects a target area for imaging;
a radiation source to emit a fan or cone of emitted radiation in radial directions towards the target area so as to irradiate a cross-section of the target area with respect to the central longitudinal axis; and
a plurality of detector arrays, each of the plurality of detector arrays including a plurality of detector segments that extend along a respective detector axis that extends in a direction that is substantially parallel to the central longitudinal axis, the plurality of detector segments being arranged such that the radiation emitted from the radiation source passes through the target area and is incident on one or more of the plurality of detector segments, wherein
each detector segment of each detector array includes a detecting surface that is tilted such that the detecting surface has a tilt with respect to the detector axis.

16. The medical imaging system of claim 15, wherein:
the plurality of detector arrays extend circularly so as to encompass only an arc of space that coincides with the fan or cone of emitted radiation, so as to encompass only a wedge portion of the frame of the medical imaging system; and
the radiation source and the plurality of detector arrays are coupled together so as rotate together about the central longitudinal axis.

17. The medical imaging system of claim 15, wherein:
the radiation source is arranged to rotate around the central longitudinal axis in a circle; and
the plurality of detector arrays extend circularly so as to encompass a full range of different alignments for the fan or cone of emitted radiation as the radiation source rotates around the central longitudinal axis in the circle, while the plurality of detector arrays remain stationary with respect to the target area.

18. The medical imaging system of claim 15, wherein the plurality of detector arrays are angularly and regularly spaced apart, such that a radial angle of a radial line that extends from the central longitudinal axis to respective detector axis changes by a constant amount between adjacent detector arrays.

19. A detector array for detecting radiation in a medical imaging system that includes a frame that has a bore, the detector array comprising:
a plurality of detector segments that extend along a detector axis that extends in a direction that is substantially parallel to a longitudinal axis of the bore of the medical imaging system, wherein
each detector segment of the plurality of detector segments includes a detecting surface that is tilted such that the detecting surface has a slope with respect to the detector axis and the longitudinal axis.

20. The detector according to claim 19, wherein the slope of detecting surfaces of adjacent detector segments of the detector array varies so that a tilt angle between the detecting surfaces varies between the adjacent detector segments in a direction along the detector axis.

* * * * *